United States Patent
Demartini et al.

(10) Patent No.: US 12,291,713 B2
(45) Date of Patent: May 6, 2025

(54) MODIFIED YEAST AND METHOD FOR INCREASING LYSINE CONTENT IN FERMENTATION CO-PRODUCTS

(71) Applicant: DANISCO US INC, Palo Alto, CA (US)

(72) Inventors: Jaclyn Diana Demartini, Palo Alto, CA (US); Celia Emily Gaby Payen, Wilmington, DE (US)

(73) Assignee: DANISCO US INC., Palo Alto, CA (US)

( * ) Notice: Subject to any disclaimer, the term of this patent is extended or adjusted under 35 U.S.C. 154(b) by 616 days.

(21) Appl. No.: 17/621,982

(22) PCT Filed: Jun. 22, 2020

(86) PCT No.: PCT/US2020/038879
§ 371 (c)(1),
(2) Date: Dec. 22, 2021

(87) PCT Pub. No.: WO2020/263720
PCT Pub. Date: Dec. 30, 2020

(65) Prior Publication Data
US 2022/0251582 A1 Aug. 11, 2022

Related U.S. Application Data

(60) Provisional application No. 62/865,457, filed on Jun. 24, 2019.

(51) Int. Cl.
| | |
|---|---|
| C12N 15/81 | (2006.01) |
| C12N 9/10 | (2006.01) |
| C12N 15/52 | (2006.01) |
| C12P 13/08 | (2006.01) |
| C12P 19/02 | (2006.01) |
| C12P 19/14 | (2006.01) |

(52) U.S. Cl.
CPC ........... *C12N 15/81* (2013.01); *C12N 9/1025* (2013.01); *C12N 15/52* (2013.01); *C12P 13/08* (2013.01); *C12P 19/02* (2013.01); *C12P 19/14* (2013.01); *C12Y 203/03014* (2013.01)

(58) Field of Classification Search
CPC ...... C12N 15/81; C12N 9/1025; C12N 15/52; C12P 13/08; C12P 19/02; C12P 19/14; C12Y 203/03014; Y02E 50/10
See application file for complete search history.

(56) References Cited

U.S. PATENT DOCUMENTS

| | | |
|---|---|---|
| 8,795,998 B2 | 8/2014 | Pronk et al. |
| 8,956,851 B2 | 2/2015 | Argyros et al. |
| 9,175,270 B2 | 11/2015 | Nevoigt et al. |

FOREIGN PATENT DOCUMENTS

| | | |
|---|---|---|
| WO | 2015/023989 A1 | 2/2015 |
| WO | 2015/148272 A1 | 10/2015 |
| WO | 2016210343 A1 | 12/2016 |

OTHER PUBLICATIONS

Guo et al., Protein tolerance to random amino acid change. PNAS., 2004, vol. 101 (25): 9205-9210. (Year: 2004).*
Sadowski et al., The sequence-structure relationship and protein function prediction. Current Opinion in Structural Biology, 2009, vol. 19: 357-362. (Year: 2009).*
Seffernick et al., Melamine deaminase and Atrazine chlorohydrolase: 98 percent identical but functionally different. J. Bacteriol., 2001, vol. 183 (8): 2405-2410. (Year: 2001).*
Tang et al., Identification of Dehalobacter reductive dehydrogenases that catalyse dechlorination of chloroform, 1,1,1-trichloroethane and 1, 1-dichloroethane. Phil Trans R Soc B, 2013, vol. 368: Mar. 18, 2012, pp. 1-10. (Year: 2013).*
Witkowski et al., Conversion of b-ketoacyl synthase to a Malonyl Decarboxylase by replacement of the active cysteine with glutamine. Biochemistry, 1999, vol. 38: 11643-11650. (Year: 1999).*
Chica et al., Semi-rational approaches to engineering enzyme activity: combining the benefits of directed evolution and rational design. Curr. Opi. Biotechnol., 2005, vol. 16: 378-384. (Year: 2005).*
Sen et al., Developments in directed evolution for enzyme functions. Appl. Biochem. Biotechnol., 2007, vol. 143: 212-223. (Year: 2007).*
RCSB PDB databank; Homocitrate Synthase, pp. 1-16, downloaded Dec. 19, 2024. (Year: 2024).*
International Search Report and Written Opinion from PCT Application No. PCT/US2020/038879 dated Sep. 7, 2020, 11 pages.
Altschul et al., "Basic Local Alignment Search Tool", J. Mol. Bio., 215, Nov. 1990, pp. 403-410.
Altschul et al., "Local alignment statistics", Methods in Enzymology, vol. 266, 1996, pp. 460-480.
Devereux et al., "A comprehensive set of sequence analysis programs for the VAX", Nucleic Acids Research, vol. 12, No. 1, 1984, pp. 387-395.
Duskova et al., "Two glycerol uptake systems contribute to the high osmotolerance of Zygosaccharomyces rouxii", Molecular Microbiology vol. 97, No. 3, 2015, pp. 541-559.
Feller et al., "In Saccharomyces cerevisae, feedback inhibition of homocitrate synthase isoenzymes by lysine modulates the activation of LYS gene expression by Lys14p", European Journal of Biochemistry, vol. 261, Issue 1, Mar. 1999, pp. 163-170.
Feng et al., "Progressive sequence alignment as a prerequisite to correct phylogenetic trees", Journal of Molecular Evolution, J Mol Evol , 25, 1987, pp. 351-360.

(Continued)

*Primary Examiner* — Ganapathirama Raghu

(57) ABSTRACT

Described are strains and methods relating to genetically-engineered yeast cells that overproduce lysine in a tunable manner by altering feedback inhibition of the lysine synthetic pathway by way of the LYS20 and LYS21 homocitrate synthase polypeptides. The yeast can be used in a conventional bioethanol production facility to produce alcohol along with increased amounts of lysine, resulting in increased quality and commercial value of fermentation products and co-products, such as animal feed ingredients.

9 Claims, No Drawings
Specification includes a Sequence Listing.

(56) References Cited

OTHER PUBLICATIONS

Ferreira et al. "A Member of the Sugar Transporter Family, Stl1p Is the Glycerol/H+ Symporter in *Saccharaomyces cerevisiae*", Molecular Biology of the Cell, vol. 16, Apr. 2005, pp. 2068-2076.

Fowler et al., "Deep mutational scanning: a new style of protein science", Nature Methods, vol. 11(8), Jul. 2014, pp. 801-807.

Gasent-Ramirez et al., "Lysine-Overproducing Mutants of Saccharyomyces cerevisiae Baker's Yeast Isolated in Continuous Culture", Applied and Environmental Microbiology, vol. 63, No. 12, Dec. 1997, pp. 4800-4806.

Henikoff et al., "Amino acid substitution matrices from protein blocks", Proc. Natl. Acad. Sci. USA, vol. 89, Nov. 1992, pp. 10915-10919.

Higgins et al., "Fast and sensitive multiple sequence alignments on a microcomputer", Bioinformatics, vol. 5, Issue 2, Apr. 1989, pp. 151-153.

Karlin et al., "Applications and statistics for multiple high-scoring segments in molecular sequences", Proc. Natl. Acad. Sci. USA, vol. 90, Jun. 1993, pp. 5873-5877.

Needleman et al., "A General Method Applicable to the Search for Similarities in the Amino Acid Sequence of Two Proteins", J. Mol. Biol., 48, 1970, pp. 443-453.

Pearson et al., "Improved tools for biological sequence comparison", Proc. Natl. Acad. Sci. USA, vol. 85, Apr. 1988, pp. 2444-2448.

Quezada et al., "The Lys20 homocitrate synthase isoform exerts most of the flux control over the lysine synthesis pathway in Saccharomyces cerevisiae: Control of alpha-amionadipate pathway flux", Molecular Biology, vol. 82, No. 3, Nov. 1, 2011, pp. 578-590.

Smith et al., "Comparison of Biosequences", Advances in Applied Mathmatics 2, 1981, pp. 482-489.

Starita et al., "Deep Mutational Scanning: Calculating Enrichment Scores for Protein Variants from DNA Sequencing Output Files", Cold Spring Harbor Protocols, Aug. 1, 2015, pp. 777-780.

Thompson et al. "Clustal W" improving the sensitivity of progressive multiple sequence alignment through sequence weighting, position-specific gap penalties and weight matrix choice, Nucleic Acids Research, vol. 22, No. 22, 1994, pp. 4673-4680.

Zumwalt et al., "Acid Hydrolysis of Proteins for Chromatographic Analysis of Amino Acids", Journal of Association of Official Analytical Chemists, vol. 70, Issue 1, Jan. 1, 1987, pp. 147-151.

Devos et al., "Practical Limits of Function Prediction", Proteins: Structure, Function, and Genetics, vol. 41, 2000, pp. 98-107.

\* cited by examiner

MODIFIED YEAST AND METHOD FOR INCREASING LYSINE CONTENT IN FERMENTATION CO-PRODUCTS

CROSS-REFERENCE TO RELATED APPLICATION

This application is a U.S. national stage application under 35 U.S.C. § 371 of International Application No. PCT/US2020/038879, filed on Jun. 22, 2020, entitled "MODIFIED YEAST AND METHOD FOR INCREASING LYSINE CONTENT IN FERMENTATION CO-PRODUCTS," which claims priority to U.S. Provisional Patent Application No. 62/865,457 filed Jun. 24, 2019, the disclosure of which is incorporated by reference herein in its entirety.

INCORPORATION BY REFERENCE OF THE SEQUENCE LISTING

The present application is being filed with a Sequence Listing in electronic format. The Sequence Listing is provided as a file entitled NB41612USPCT_SeqList.txt, created on Nov. 18, 2021, which is 11,943 bytes in size. The information in the electronic format of the Sequence Listing is incorporated by reference in its entirety.

TECHNICAL FIELD

The present strains and methods relate to genetically-engineered yeast cells that overproduce lysine in a tunable manner by altering feedback inhibition of the lysine synthetic pathway by way of the LYS20 and LYS21 homocitrate synthase polypeptides. The yeast can be used in a conventional bioethanol production facility to produce alcohol along with increased amounts of lysine, resulting in increased quality and commercial value of fermentation products and co-products, such as animal feed ingredients.

BACKGROUND

Many countries make fuel alcohol from fermentable substrates, such as corn starch, sugar cane, cassava, and molasses. According to the Renewable Fuel Association (Washington DC, United States), 2015 fuel ethanol production was close to 15 billion gallons in the United States, alone.

In addition to producing about 2.8 gallons of ethanol, a 56-pound bushel of corn processed in a dry mill ethanol plant also generates about 17.5 pounds of animal feed. Animal feed is usually in the form of distillers dried grains with solute (DDGS) and represents the starch-depleted portion of corn plus the biomass of the yeast used for fermentation. Per weight, DDGS is more nutritional for animals than the unprocessed corn because it is richer in protein and fat. Beyond DDGS, dry mill ethanol plants also have the ability to create other protein-rich corn co-products for animal feed applications.

Lysine is an essential amino acid for most animals and must be supplemented if it cannot be supplied in adequate amounts in DDGS to meet feed conversion expectations. Synthetic lysine is expensive and can represent a significant cost of animal feed. The need exists for ways to improve or maintain the production of alcohol from starch-containing feedstocks while increasing the nutritional value of animal feed co-products.

SUMMARY

Described are compositions and methods relating to yeast cells having a genetic mutation that increases lysine production in yeast, result in ethanol fermentation products and co-products having increased nutritional value. Aspects and embodiments of the compositions and methods are described in the following, independently-numbered paragraphs.

1. In one aspect, a non-naturally-occurring variant homocitrate synthase polypeptide is provided, having at least 80% amino acid sequence identity to SEQ ID NO: 2 and comprising one or more mutations selected from the group consisting of F36Y, N38K, N289D R349K, Q352E, V375D, R376T and I380M, with respect to SEQ ID NO: 2, wherein the variant homocitrate synthase polypeptide demonstrates reduced lysine inhibition compared to an otherwise identical homocitrate synthase polypeptide lacking the one or more mutations.

2. In some embodiments of the non-naturally-occurring variant homocitrate synthase polypeptide of paragraph 1, the one or more mutations are F36Y and N38K.

3. In a related aspect, a non-naturally-occurring variant homocitrate synthase polypeptide is provided, having at least 80% amino acid sequence identity to SEQ ID NO: 1 and comprising one or more mutations selected from the group consisting of N52D, D125N, R289I, N303D and N393D, with respect to SEQ ID NO: 1, wherein the variant homocitrate synthase polypeptide demonstrates reduced lysine inhibition compared to an otherwise identical homocitrate synthase polypeptide lacking the one or more mutations.

4. In another aspect, yeast cells producing the variant homocitrate synthase polypeptide of any of paragraphs 1-3 are provided.

5. In some embodiments of the yeast cells of paragraph 4, the cells are of a *Saccharomyces* spp.

6. In some embodiments of the yeast cells of paragraph 4 or 5, the cells further comprise one or more genes of the phosphoketolase pathway.

7. In some embodiments of the yeast cells of paragraph 6, the genes of the phosphoketolase pathway are selected from the group consisting of phosphoketolase, phosphotransacetylase and acetylating acetyl dehydrogenase.

8. In some embodiments of the yeast cells of any of paragraphs 4-7, the cells further comprise an exogenous gene encoding a carbohydrate processing enzyme.

9. In some embodiments, the yeast cells of any of paragraphs 4-8, further comprise an alteration in the glycerol pathway and/or the acetyl-CoA pathway.

10. In some embodiments, the yeast cells of any of paragraphs 4-9, further comprise an alternative pathway for making ethanol.

11. In another aspect, a method for increasing the amount of lysine present in a post-fermentation product from an ethanol production facility is provided, comprising: (i) hydrolyzing a starch-containing feedstock with an α-amylase to produce a starch liquefact; (ii) saccharifying the starch liquefact with a glucoamylase to produce glucose; (iii) fermenting the glucose with modified yeast cells derived from parental yeast cells, the modified yeast cells comprising a genetic alteration that reduces feedback inhibition of the lysine production pathway as mediated through homocitrate synthase polypeptides in the lysine production pathway; and (iv) recovering post-fermentation by-product enriched for lysine compared to post-fermentation by-products recovered from an otherwise identical process using the parental yeast.

12. In some embodiments of the method of paragraph 11, the post-fermentation product is selected from the group consisting of fermentation broth, whole stillage, thin stillage, distillers dried grains, distillers dried grains with solutes, condensed distillers solubles or other protein-containing coproducts.

13. In some embodiments of the method of paragraph 11 or 12, one or more steps (i)-(iv) are combined, simultaneous or over-lapping.

14. In another aspect, a method for increasing the amount of lysine present in a fermentation product is provided, comprising: (i) fermenting glucose or another sugar with modified yeast cells derived from parental yeast cells, the modified yeast cells comprising a genetic alteration that reduces feedback inhibition of the lysine production pathway as mediated through homocitrate synthase polypeptides in the lysine production pathway; and (ii) recovering fermentation product enriched for lysine compared to a fermentation product recovered from an otherwise identical process using the parental yeast.

15. In some embodiments of the method of any of paragraphs 11-14, fermenting the glucose with the modified yeast cells is performed in the further presence of the parental yeast cells or of conventional yeast cells.

16. In some embodiments of the method of paragraph 15, fermenting the glucose with the modified yeast cells in the further presence of the parental yeast cells or of conventional yeast cells is performed by adding the modified yeast cells and the parental or conventional yeast cells to a fermenter at different times.

17. In some embodiments of the method of any of paragraphs 11-16, the homocitrate synthase polypeptides are LYS20 and/or LYS21.

18. In some embodiments of the method of paragraph 17, the modified yeast produces an altered amount of LYS20 and/or LYS21 polypeptide compared to otherwise identical yeast.

19. In some embodiments of the method of paragraph 17, the modified yeast produces a variant LYS20 and/or LYS21 polypeptide compared to otherwise identical yeast.

20. In some embodiments of the method of any of paragraphs 11-19, the modified yeast is the yeast of any of paragraphs 1-10.

21. In another aspect, a post-fermentation product produced by the method of any of paragraphs 11-20 is provided.

22. In another aspect, a composition or method having any of the features of paragraphs 1-22 or features mentioned in the description is provided.

These and other aspects and embodiments of present modified cells and methods will be apparent from the description, including any accompanying FIGURES.

DETAILED DESCRIPTION

I. Overview

Described are methods relating to yeast having a genetic mutation that reduced the amount of feedback inhibition in the lysine synthetic pathway by way of the LYS20 and LYS21 homocitrate synthase polypeptides. The yeast can be used in a conventional bioethanol production facility to produce alcohol along with increased amounts of lysine, resulting in increased quality and commercial value of fermentation products and co-products, such as animal feed ingredients.

II. Definitions

Prior to describing the present strains and methods in detail, the following terms are defined for clarity. Terms not defined should be accorded their ordinary meanings as used in the relevant art.

As used herein, "alcohol" refers to an organic compound in which a hydroxyl functional group (—OH) is bound to a saturated carbon atom.

As used herein, the phrase "degree of polymerization" (DP) refers to the number (n) of anhydroglucopyranose units in a given saccharide. Examples of DP1 are the monosaccharides glucose and fructose. Examples of DP2 are the disaccharides maltose and sucrose. The meaning of DP1, DP12, DP3, DP4, DP4+ etc. is well known in science of carbohydrate processing.

As used herein, "yeast cells" yeast strains, or simply "yeast" refer to organisms from the phyla Ascomycota and Basidiomycota. Exemplary yeast is budding yeast from the order Saccharomycetales. Particular examples of yeast are *Saccharomyces* spp., including but not limited to *S. cerevisiae*. Yeast include organisms used for the production of fuel alcohol as well as organisms used for the production of potable alcohol, including specialty and proprietary yeast strains used to make distinctive-tasting beers, wines, and other fermented beverages.

As used herein, the phrase "variant yeast cells," "modified yeast cells," or similar phrases (see above), refer to yeast that include genetic modifications and characteristics described herein. Variant/modified yeast do not include naturally occurring yeast.

As used herein, the phrase "substantially free of an activity," or similar phrases, means that a specified activity is either undetectable in an admixture or present in an amount that would not interfere with the intended purpose of the admixture.

As used herein, the terms "polypeptide" and "protein" (and their respective plural forms) are used interchangeably to refer to polymers of any length comprising amino acid residues linked by peptide bonds. The conventional one-letter or three-letter codes for amino acid residues are used herein and all sequence are presented from an N-terminal to C-terminal direction. The polymer can be linear or branched, it can comprise modified amino acids, and it can be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art.

As used herein, functionally and/or structurally similar proteins are considered to be "related proteins." Such proteins can be derived from organisms of different genera and/or species, or even different classes of organisms (e.g., bacteria and fungi). Related proteins also encompass homologs determined by primary sequence analysis, determined by secondary or tertiary structure analysis, or determined by immunological cross-reactivity.

As used herein, the term "homologous protein" refers to a protein that has similar activity and/or structure to a reference protein. It is not intended that homologs necessarily be evolutionarily related. Thus, it is intended that the term encompass the same, similar, or corresponding enzyme(s) (i.e., in terms of structure and function) obtained from different organisms. In some embodiments, it is desirable to identify a homolog that has a quaternary, tertiary and/or primary structure similar to the reference protein. In some embodiments, homologous proteins induce similar immunological response(s) as a reference protein. In some embodiments, homologous proteins are engineered to produce enzymes with desired activity(ies).

The degree of homology between sequences can be determined using any suitable method known in the art (see, e.g., Smith and Waterman (1981) *Adv. Appl. Math.* 2:482; Needleman and Wunsch (1970) *J. Mol. Biol.,* 48:443; Pearson and Lipman (1988) *Proc. Natl. Acad. Sci. USA* 85:2444; programs such as GAP, BESTFIT, FASTA, and TFASTA in the Wisconsin Genetics Software Package (Genetics Computer Group, Madison, WI); and Devereux et al. (1984) *Nucleic Acids Res.* 12:387-95).

For example, PILEUP is a useful program to determine sequence homology levels. PILEUP creates a multiple sequence alignment from a group of related sequences using progressive, pair-wise alignments. It can also plot a tree showing the clustering relationships used to create the alignment. PILEUP uses a simplification of the progressive alignment method of Feng and Doolittle, (Feng and Doolittle (1987) *J. Mol. Evol.* 35:351-60). The method is similar to that described by Higgins and Sharp ((1989) *CABIOS* 5:151-53). Useful PILEUP parameters including a default gap weight of 3.00, a default gap length weight of 0.10, and weighted end gaps. Another example of a useful algorithm is the BLAST algorithm, described by Altschul et al. ((1990) *J. Mol. Biol.* 215:403-10) and Karlin et al. ((1993) *Proc. Natl. Acad. Sci. USA* 90:5873-87). One particularly useful BLAST program is the WU-BLAST-2 program (see, e.g., Altschul et al. (1996) *Meth. Enzymol.* 266:460-80). Parameters "W," "T," and "X" determine the sensitivity and speed of the alignment. The BLAST program uses as defaults a word-length (W) of 11, the BLOSUM62 scoring matrix (see, e.g., Henikoff and Henikoff (1989) *Proc. Natl. Acad. Sci. USA* 89:10915) alignments (B) of 50, expectation (E) of 10, M'5, N'-4, and a comparison of both strands.

As used herein, the phrases "substantially similar" and "substantially identical," in the context of at least two nucleic acids or polypeptides, typically means that a polynucleotide or polypeptide comprises a sequence that has at least about 70% identity, at least about 75% identity, at least about 80% identity, at least about 85% identity, at least about 90% identity, at least about 91% identity, at least about 92% identity, at least about 93% identity, at least about 94% identity, at least about 95% identity, at least about 96% identity, at least about 97% identity, at least about 98% identity, or even at least about 99% identity, or more, compared to the reference (i.e., wild-type) sequence. Percent sequence identity is calculated using CLUSTAL W algorithm with default parameters. See Thompson et al. (1994) *Nucleic Acids Res.* 22:4673-4680. Default parameters for the CLUSTAL W algorithm are:

Gap opening penalty: 10.0
Gap extension penalty: 0.05
Protein weight matrix: BLOSUM series
DNA weight matrix: IUB
Delay divergent sequences %: 40
Gap separation distance: 8
DNA transitions weight: 0.50
List hydrophilic residues: GPSNDQEKR
Use negative matrix: OFF
Toggle Residue specific penalties: ON
Toggle hydrophilic penalties: ON
Toggle end gap separation penalty OFF.

Another indication that two polypeptides are substantially identical is that the first polypeptide is immunologically cross-reactive with the second polypeptide. Typically, polypeptides that differ by conservative amino acid substitutions are immunologically cross-reactive. Thus, a polypeptide is substantially identical to a second polypeptide, for example, where the two peptides differ only by a conservative substitution. Another indication that two nucleic acid sequences are substantially identical is that the two molecules hybridize to each other under stringent conditions (e.g., within a range of medium to high stringency).

As used herein, the term "gene" is synonymous with the term "allele" in referring to a nucleic acid that encodes and directs the expression of a protein or RNA. Vegetative forms of filamentous fungi are generally haploid, therefore a single copy of a specified gene (i.e., a single allele) is sufficient to confer a specified phenotype.

As used herein, the terms "wild-type" and "native" are used interchangeably and refer to genes proteins or strains found in nature.

As used herein, the term "protein of interest" refers to a polypeptide that is desired to be expressed in modified yeast. Such a protein can be an enzyme, a substrate-binding protein, a surface-active protein, a structural protein, a selectable marker, or the like, and can be expressed at high levels. The protein of interest is encoded by a modified endogenous gene or a heterologous gene (i.e., gene of interest") relative to the parental strain. The protein of interest can be expressed intracellularly or as a secreted protein.

As used herein, "deletion of a gene," refers to its removal from the genome of a host cell. Where a gene includes control elements (e.g., enhancer elements) that are not located immediately adjacent to the coding sequence of a gene, deletion of a gene refers to the deletion of the coding sequence, and optionally adjacent enhancer elements, including but not limited to, for example, promoter and/or terminator sequences, but does not require the deletion of non-adjacent control elements.

As used herein, "disruption of a gene" refers broadly to any genetic or chemical manipulation, i.e., mutation, that substantially prevents a cell from producing a function gene product, e.g., a protein, in a host cell. Exemplary methods of disruption include complete or partial deletion of any portion of a gene, including a polypeptide-coding sequence, a promoter, an enhancer, or another regulatory element, or mutagenesis of the same, where mutagenesis encompasses substitutions, insertions, deletions, inversions, and combinations and variations, thereof, any of which mutations substantially prevent the production of a function gene product. A gene can also be disrupted using RNAi, antisense, or any other method that abolishes gene expression. A gene can be disrupted by deletion or genetic manipulation of non-adjacent control elements.

As used herein, the terms "genetic manipulation" and "genetic alteration" are used interchangeably and refer to the alteration/change of a nucleic acid sequence. The alteration can include but is not limited to a substitution, deletion, insertion or chemical modification of at least one nucleic acid in the nucleic acid sequence.

As used herein, a "primarily genetic determinant" refers to a gene, or genetic manipulation thereof, that is necessary and sufficient to confer a specified phenotype in the absence of other genes, or genetic manipulations, thereof. However, that a particular gene is necessary and sufficient to confer a specified phenotype does not exclude the possibility that additional effects to the phenotype can be achieved by further genetic manipulations.

As used herein, a "functional polypeptide/protein" is a protein that possesses an activity, such as an enzymatic activity, a binding activity, a surface-active property, or the like, and which has not been mutagenized, truncated, or otherwise modified to abolish or reduce that activity. Functional polypeptides can be thermostable or thermolabile, as specified.

As used herein, "a functional gene" is a gene capable of being used by cellular components to produce an active gene product, typically a protein. Functional genes are the antithesis of disrupted genes, which are modified such that they cannot be used by cellular components to produce an active gene product, or have a reduced ability to be used by cellular components to produce an active gene product.

As used herein, yeast cells have been "modified to prevent the production of a specified protein" if they have been genetically or chemically altered to prevent the production of a functional protein/polypeptide that exhibits an activity characteristic of the wild-type protein. Such modifications include, but are not limited to, deletion or disruption of the gene encoding the protein (as described, herein), modification of the gene such that the encoded polypeptide lacks the aforementioned activity, modification of the gene to affect post-translational processing or stability, and combinations, thereof.

As used herein, "fermentation broth" is the product of an ethanol production facility following fermentation with yeast but prior to distillation.

As used herein, "whole stillage" is the byproduct an ethanol production facility following distillation.

As used herein, "thin stillage" is the liquid portion of whole stillage following separation of solid materials.

As used herein, "distillers' grains (DG)" is the solid/slurry component of whole stillage.

As used herein, "distillers' dried grains (DDG) is DG that have been dried.

As used herein, "distillers' dried grains with solutes (DDGS) is DG that has been dried along with the concentrated thin stillage for added nutritional value.

As used herein, a "wet" by-product of distillation contains at least 20% water by weight.

As used herein, a "dried" by-product of distillation contains less than 20% water by weight.

As used herein, "aerobic fermentation" refers to growth in the presence of oxygen.

As used herein, "anaerobic fermentation" refers to growth in the absence of oxygen.

As used herein, the singular articles "a," "an," and "the" encompass the plural referents unless the context clearly dictates otherwise. All references cited herein are hereby incorporated by reference in their entirety. The following abbreviations/acronyms have the following meanings unless otherwise specified:

° C. degrees Centigrade
DG distillers' grains
DDG distillers' dried grains
DDGS distillers' dried grains with solutes
DNA deoxyribonucleic acid
DP degree of polymerization
DS dry solids
EtOH ethanol
g or gm gram
g/L grams per liter
GA glucoamylase
GAU/g DS glucoamylase units per gram dry solids
HPLC high performance liquid chromatography
hr or h hour
kDa kilodalton
M molar
mg milligram
mL or ml milliliter
ml/min milliliter per minute
mM millimolar
N normal
na not applicable
PCR polymerase chain reaction
ppm parts per million
SAPU/g DS protease units per gram dry solids
SSCU/g DS fungal α-amylase units per gram dry solids
Δ relating to a deletion
μg microgram
μL and μl microliter
μM and μm micromolar
AEC aminoethylcysteine

III. Yeast Cells Having Reduced Feedback Inhibition of the Lysine Biosynthetic Pathway The lysine biosynthetic pathway in *Saccharomyces cerevisiae* and other yeast is characterized by product feedback inhibition by the interaction of lysine with two nuclear homocitrate synthase isoenzymes, referred to as LYS20 and LYS21. The isoforms responds to lysine with different sensitivities. Mutant yeast having alterations in the amino acid sequence of LYS20 and LYS21, which result in reduced sensitivity to lysine feedback, have been described (Feller et al. (1999) *Eur. J. Biochem.* 261:163-170).

The present compositions and methods are based on the discovery that yeast desensitized for lysine feedback inhibition represent an effective way to significantly improve the quality of animal feed co-products generated by commercial ethanol production facilities. The ability to substantially increase the amount of lysine in, e.g., distillers dried grains with solutes (DDGS), means that less synthetic lysine is needed to supplement animal feed products, resulting in significant cost savings to ranchers and farmers.

Described are mutations in LYS20 and LYS21 that result in up to greater than 350-fold increased free lysine content in yeast, which can be expected to produce up to a 100-fold increase in lysine in animal feed co-products, such as fermentation broth, whole stillage, thin stillage, distillers dried grains, distillers dried grains with solutes, condensed distillers solubles or other protein-containing coproducts In some embodiments, desensitization to lysine feedback inhibition is achieved by over-expressing LYS20 and LYS21, such that the cells cannot make a sufficient amount of lysine to repress all the LYS20 and LYS21 in the nucleus. In preferred embodiments, yeast is modified to produce variant LYS20 and LYS21 polypeptides. As described herein, variant polypeptides can be selected to tailor, or "tune," lysine over-production to a particular application by selecting a particular variant LYS20 and LYS21 variant that allows for only a few-fold lysine over-production or hundreds-of-fold over-production.

Lysine-overproduction is expected to compete with alcohol production, so the ability to select how much carbon is diverted to lysine is important to commercial alcohol producers. Using the present yeast, producers can select how much carbon to direct to lysine simply by batching a different yeast in a fermenter. Producers may also choose to add the present yeast and more conventional yeast to a fermenter at different times, or at different ratios, to further fine tune the production of alcohol and lysine.

In some embodiments of the present compositions and methods, the yeast produces a variant LYS20 polypeptide having at least 80%, at least 85% at least 90%, at least 95%, at least 97%, at least 98%, at least 99%, but less than 100%, to the amino acid of SEQ ID NO: 2, and comprising one or more mutations selected from the group consisting of F36Y, N38K, N289D R349K, Q352E, V375D, R376T and I380M, with respect to SEQ ID NO: 2. In a particular embodiment, the mutations are F36Y and N38K. In some embodiments of the present compositions and methods, the yeast produces a variant LYS20 LYS21 polypeptide having at least 80%, at least 85% at least 90%, at least 95%, at least 97%, at least 98%, at least 99%, but less than 100%, to the amino acid of SEQ ID NO: 1, and comprising one or more mutations selected from the group consisting of N52D, D125N, R289I, N303D and N393D, with respect to SEQ ID NO: 1.

In some embodiments, the modified cells include other genes or other modifications that increase lysine production.

IV. Combination of Decreased Lysine Feedback Inhibition with Mutations that Benefit Alcohol Production In some embodiments, in addition to having reducing feedback inhibition in the lysine biosynthetic pathway by way of LYS20 and/or LYS21, the present modified yeast cells further include additional modifications that benefit alcohol production.

In particular embodiments the modified yeast cells include an artificial or alternative ethanol-producing pathway resulting from the introduction of a heterologous phosphoketolase (PKL) gene, a heterologous phosphotransacetylase (PTA) gene and a heterologous acetylating acetyl dehydrogenase (AADH), as described in WO2015148272 (Miasnikov et al.), to channel carbon flux away from the glycerol pathway and toward the synthesis of acetyl-CoA, which is then converted to ethanol.

The modified cells may further include mutations that result in attenuation of the native glycerol biosynthesis pathway, which are known to increase alcohol production. Methods for attenuation of the glycerol biosynthesis pathway in yeast are known and include reduction or elimination of endogenous NAD-dependent glycerol 3-phosphate dehydrogenase (GPD) or glycerol phosphate phosphatase activity (GPP), for example by disruption of one or more of the genes GPD1, GPD2, GPP1 and/or GPP2. See, e.g., U.S. Pat. No. 9,175,270 (Elke et al.), U.S. Pat. No. 8,795,998 (Pronk et al.) and U.S. Pat. No. 8,956,851 (Argyros et al.).

The modified yeast may further feature increased acetyl-CoA synthase (also referred to acetyl-CoA ligase) activity (EC 6.2.1.1) to scavenge (i.e., capture) acetate produced by chemical or enzymatic hydrolysis of acetyl-phosphate (or present in the culture medium of the yeast for any other reason) and converts it to Ac-CoA. This avoids the undesirable effect of acetate on the growth of yeast cells and may further contribute to an improvement in alcohol yield. Increasing acetyl-CoA synthase activity may be accomplished by introducing a heterologous acetyl-CoA synthase gene into cells, increasing the expression of an endogenous acetyl-CoA synthase gene and the like. A particularly useful acetyl-CoA synthase for introduction into cells can be obtained from *Methanosaeta concilii* (UniProt/TrEMBL Accession No.: WP_013718460). Homologs of this enzymes, including enzymes having at least 85%, at least 90%, at least 92%, at least 95%, at least 97%, at least 98% and even at least 99% amino acid sequence identity to the aforementioned acetyl-CoA synthase from *Methanosaeta concilii*, are also useful in the present compositions and methods.

In some embodiments the modified cells may further include a heterologous gene encoding a protein with NAD$^+$-dependent acetylating acetaldehyde dehydrogenase activity and/or a heterologous gene encoding a pyruvate-formate lyase. The introduction of such genes in combination with attenuation of the glycerol pathway is described, e.g., in U.S. Pat. No. 8,795,998 (Pronk et al.).

In some embodiments, the present modified yeast cells may further overexpress a sugar transporter-like (STL1) polypeptide (see, e.g., Ferreira et al. (2005) *Mol Biol Cell* 16:2068-76; Dušková et al. (2015) *Mol Microbiol* 97:541-59 and WO 2015023989 A1) to increase ethanol production and reduce acetate.

In some embodiments, the present modified yeast cells may further overexpress a polyadenylate-binding protein, e.g., PAB1, to increase alcohol production and reduce acetate production.

In some embodiments, the present modified yeast cells further comprise a butanol biosynthetic pathway. In some embodiments, the butanol biosynthetic pathway is an isobutanol biosynthetic pathway. In some embodiments, the isobutanol biosynthetic pathway comprises a polynucleotide encoding a polypeptide that catalyzes a substrate to product conversion selected from the group consisting of: (a) pyruvate to acetolactate; (b) acetolactate to 2,3-dihydroxyisovalerate; (c) 2,3-dihydroxyisovalerate to 2-ketoisovalerate; (d) 2-ketoisovalerate to isobutyraldehyde; and (e) isobutyraldehyde to isobutanol. In some embodiments, the isobutanol biosynthetic pathway comprises polynucleotides encoding polypeptides having acetolactate synthase, keto acid reductoisomerase, dihydroxy acid dehydratase, ketoisovalerate decarboxylase, and alcohol dehydrogenase activity.

In some embodiments, the modified yeast cells comprising a butanol biosynthetic pathway further comprise a modification in a polynucleotide encoding a polypeptide having pyruvate decarboxylase activity. In some embodiments, the yeast cells comprise a deletion, mutation, and/or substitution in an endogenous polynucleotide encoding a polypeptide having pyruvate decarboxylase activity. In some embodiments, the polypeptide having pyruvate decarboxylase activity is selected from the group consisting of: PDC1, PDC5, PDC6, and combinations thereof. In some embodiments, the yeast cells further comprise a deletion, mutation, and/or substitution in one or more endogenous polynucleotides encoding FRA2, ALD6, ADH1, GPD2, BDH1, and YMR226C.

V. Combination of Decreased Lysine Feedback Inhibition with Other Beneficial Mutations In some embodiments, in addition to having reducing feedback inhibition in the lysine biosynthetic pathway by way of LYS20 and/or LYS21, optionally in combination with genetic modifications that benefit alcohol production, the present modified yeast cells further include any number of additional genes of interest encoding proteins of interest. Additional genes of interest may be introduced before, during, or after genetic manipulations that result in reduced lysine feedback inhibition or increased alcohol production. Proteins of interest, include selectable markers, carbohydrate-processing enzymes, and other commercially-relevant polypeptides, including but not limited to an enzyme selected from the group consisting of a dehydrogenase, a transketolase, a phosphoketolase, a transaldolase, an epimerase, a phytase, a xylanase, a β-glucanase, a phosphatase, a protease, an α-amylase, a β-amylase, a glucoamylase, a pullulanase, an isoamylase, a cellulase, a trehalase, a lipase, a pectinase, a polyesterase, a cutinase, an oxidase, a transferase, a reductase, a hemicellulase, a mannanase, an esterase, an isomerase, a pectinases, a lactase, a peroxidase and a laccase. Proteins of interest may be secreted, glycosylated, and otherwise-modified.

VI. Yeast Cells Suitable for Modification

Yeasts are unicellular eukaryotic microorganisms classified as members of the fungus kingdom and include organisms from the phyla Ascomycota and Basidiomycota. Yeast that can be used for alcohol production include, but are not limited to, *Saccharomyces* spp., including *S. cerevisiae*, as well as *Kluyveromyces, Lachancea* and *Schizosaccharomyces* spp. Numerous yeast strains are commercially available, many of which have been selected or genetically engineered for desired characteristics, such as high alcohol production, rapid growth rate, and the like. Numerous yeast have been genetically engineered to produce heterologous enzymes or even to include heterologous pathways. Any yeast that have homologs of LYS20 and/or LYS21 in a lysine biosynthetic pathway are believed to be candidates for modification as described.

VII. Substrates and Conditions

Alcohol production from a number of carbohydrate substrates, including but not limited to corn starch, sugar cane, cassava, and molasses, is well known, as are innumerable variations and improvements to enzymatic and chemical conditions and mechanical processes. The present compositions and methods are believed to be fully compatible with such substrates and conditions.

Numerous variations of ethanol production process exist, including cold cook, or no cook, involving liquefaction at or below the gelatinization temperature, simultaneous saccharification and fermentation, fractionation processes, and the like. None are expected to be incompatible with the present compositions and methods.

VIII. Fermentation Products and Co-Products

Typical alcohol fermentation products include organic compound having a hydroxyl functional group (—OH) is bound to a carbon atom. Exemplary alcohols include but are not limited to methanol, ethanol, n-propanol, isopropanol, n-butanol, isobutanol, n-pentanol, 2-pentanol, isopentanol, and higher alcohols. The most commonly made fuel alcohols are ethanol, and butanol.

Valuable by-products (or co-products) of alcohol production, and particularly dry-grind ethanol production, are products for animal feed, usually in the form of distillers' dried grains (DDG) or, more commonly, distillers' dried grains with solutes (DDGS). Such animal feed products are in many ways more nutritional than the initial feed-stocks used for ethanol production as they are depleted for carbohydrates but enriched for amino acids derived both from the feedstock and the fermenting organism (i.e., ethanologen).

The specific amino acid composition of DDGS or other corn co-product is important to the quality of animal feed as some amino acids are far more important than others. Lysine is an essential amino acid for most farm animals and, if not provided in adequate amounts by adequately by DDG, DDGS, or other post fermentation co-products, must be supplemented to maximize feed conversion. Synthetic lysine is expensive and represents a significant cost of animal feed.

Because yeast represent a significant component of post-fermentation products, the amino acid content of the yeast significantly affects the amino acid content of fermentation broth, whole stillage, thin stillage, distillers dried grains, distillers dried grains with solutes, condensed distillers solubles or other protein-containing post fermentation coproducts. Replacing convention yeast with the present yeast increases the amounts of lysine in such post-fermentation products, thereby increasing their value as animal feed products. Using the present modified yeast, an increase in lysine of at least 2-fold, at least 5-fold, at least 10-fold, at least 20-fold, at least 50-fold, at least 100-fold, or more, can be realized.

These and other aspects and embodiments of the present strains and methods will be apparent to the skilled person in view of the present description. The following examples are intended to further illustrate, but not limit, the strains and methods.

EXAMPLES

Example 1: Increased Production of Lysine by Yeast Expressing Variant LYS20 Polypeptides Using standard molecular biology techniques, error-prone PCR was used to create thousands of random mutations in the *Saccharomyces cerevisiae* gene YDL182w encoding the homocitrate synthase polypeptide LYS20. The resulting library of variant genes was transformed into a FERMAX® Gold yeast (Martrex, Inc., Chaska, MN, USA; herein "FG"), a well-known *S. cerevisiae* strain used for fuel ethanol production, in which the native gene encoding LYS20 was deleted, resulting in LYS20⁻ FG). Transformants were allowed to compete as a pool in minimum growth media supplemented with increased concentration of lysine toxic analog (aminoethylcysteine; AEC) up to 100 mM. Following selection, the culture was subjected to centrifugation to recover viable cells, genomic DNA was extracted, and PCR was performed to amplify variant genes encoding variant LYS20 polypeptides. Following targeted-gene sequencing using the Illumina platform, sequencing reads were mapped to the native sequence using standard mapping tools and mutations, and their relative frequency, were analyzed (see, e.g., Fowler, D. M. and Fields, S. (2014) *Nat. Methods* 11:801-07 and Starita, L. M. and Fields, S. (2015) *Cold Spring Harb Protoc.* 2015:777-80).

Procedures were based on the nucleic acid sequence of YDL182w (LYS20, chr IV: 133437 . . . 134723), show below as SEQ ID NO: 4:

```
ATGACTGCTGCTAAACCAAATCCATATGCTGCCAA

ACCGGGCGACTATCTTTCTAATGTAAATAATTTCC

AGTTAATCGATTCGACGCTGAGAGAAGGTGAACAA

TTTGCCAACGCATTCTTCGATACTGAAAAAAAGAT

CGAAATTGCTAGAGCCTTGGACGATTTCGGTGTGG

ACTACATCGAGTTAACCTCACCAGTAGCATCTGAA

CAATCAAGAAAGGACTGTGAAGCTATATGTAAACT

AGGTTTAAAGGCCAAGATCCTTACACACATTCGTT

GTCATATGGATGACGCCAAAGTCGCCGTAGAGACT

GGTGTCGACGGTGTCGATGTCGTTATCGGCACCTC

CAAATTTTTAAGACAATATTCCCACGGTAAGGATA
```

```
TGAACTACATCGCCAAGAGTGCTGTTGAAGTCATT

GAATTTGTCAAATCCAAAGGTATTGAAATCAGATT

TTCCTCTGAAGATTCCTTCAGAAGTGATCTCGTTG

ATCTTTTGAACATTTATAAAACCGTTGACAAGATC

GGTGTAAATAGAGTCGGTATTGCCGACACAGTTGG

ATGTGCCAACCCAAGACAAGTATATGAACTGATCA

GAACTTTGAAGAGTGTTGTTTCATGTGACATCGAA

TGCCATTTCCACAACGATACTGGTTGTGCCATCGC

AAACGCCTACACTGCTTTGGAAGGTGGTGCCAGAT

TGATTGACGTCAGTGTACTGGGTATTGGTGAAAGA

AACGGTATCACTCCTCTAGGTGGGCTCATGGCAAG

AATGATTGTTGCCGCACCAGACTATGTCAAGTCCA

AATACAAGTTGCACAAGATCAGAGACATTGAAAAC

CTGGTCGCTGATGCTGTGGAAGTTAACATTCCATT

CAACAACCCTATCACCGGGTTCTGTGCATTCACAC

ATAAAGCAGGTATCCATGCCAAGGCCATTTTGGCT

AACCCATCTACCTACGAAATCTTGGACCCTCACGA

TTTCGGTATGAAGAGGTATATCCACTTCGCCAACA

GACTAACTGGCTGGAACGCCATCAAAGCCAGAGTC

GACCAGTTGAACTTGAATTTGACAGATGACCAAAT

CAAGGAAGTTACTGCTAAGATTAAGAAGCTGGGTG

ATGTCAGATCGCTGAATATCGATGATGTTGACTCT

ATCATCAAGAACTTCCACGCAGAGGTCAGCACTCC

TCAAGTACTATCTGCAAAAAAGAACAAGAAGAATG

ACAGCGATGTACCGGAACTGGCCACCATCCCCGCC

GCCAAGCGGACTAAGCCATCCGCCTAA
```

YDL182w encodes the homocitrate synthase polypeptide LYS20 (Genbank Accession No. NP_010099) shown below as SEQ ID NO: 2:

```
MTAAKPNPYA AKPGDYLSNV NNFQLIDSTL

REGEQFANAF FDTEKKIEIA RALDDFGVDY

IELTSPVASE QSRKDCEAIC KLGLKAKILT

HIRCHMDDAK VAVETGVDGV DVVIGTSKFL

RQYSHGKDMN YIAKSAVEVI EFVKSKGIEI

RFSSEDSFRS DLVDLLNIYK TVDKIGVNRV

GIADTVGCAN PRQVYELIRT LKSVVSCDIE

CHFHNDTGCA IANAYTALEG GARLIDVSVL

GIGERNGITP LGGLMARMIV AAPDYVKSKY

KLHKIRDIEN LVADAVEVNI PFNNPITGFC

AFTHKAGIHA KAILANPSTY EILDPHDFGM

KRYIHFANRL TGWNAIKARV DQLNLNLTDD

QIKEVTAKIK KLGDVRSLNI DDVDSIIKNF

HAEVSTPQVL SAKKNKKNDS DVPELATIPA

AKRTKPSA
```

For initial screening, 40% of the mutational space was explored and the enrichment score (E-score) change of each mutation in the data set was determined. Top-scoring mutations, i.e., the mutations most over-represented in the population of yeast capable of growing in the presence of the lysine toxic analog, are summarized in Table 1. Mutations with lower E-scores are not shown.

TABLE 1

Mean E-score change of top LYS20 variants tolerant to lysine toxic analog

| Mutation | Average E |
| --- | --- |
| N289 to D, H, I, K, S orT | 2.12 |
| Q352 to E, H, K, L or R | 1.64 |
| I380 to M, N or T | 1.56 |
| V375 to F, G or D | 1.52 |
| N38 to D, H, I, K, T or Y | 1.51 |
| R376 to T, S or I | 1.026 |

Genes encoding eight, single-position variants, and one combinatorial variant were individually introduced into fresh LYS20⁻ FG. Transformants were grown in poor media containing proline as the nitrogen source (Gasent-Ramirez, J. M. and Benitez, T. (1997) *Applied and Environmental Microbiology* 63:4800-4806) for 26 hr. Samples were analyzed for L-lysine content following derivatization using o-phthalaldehyde and measurement of derivatized lysine detected by HPLC (Agilent Technologies 1260) using an Eclipse Plus C18 column (4.6×150 mm, 3.5-Micron) at 40° C. in a gradient of phosphate buffer, pH 7.8 and acetonitrile:methanol:water (45:45:10). Calibration standards used for quantification included known amounts lysine or a standard amino acid mixture (Agilent Technologies) including known amounts of L-Lysine.

As shown in Table 2, yeast expressing variant LYS20 polypeptides produced a wide-ranging, 2.7 to 33-fold increase in free intracellular lysine compared to the amount produced by the unmodified reference strain.

TABLE 2

Free intracellular lysine produced by in individual variant LYS20 transformants

| Mutation(s) | Fold increase |
| --- | --- |
| FG | na |
| F36Y | 2.91 |
| N38K | 3.27 |
| N289D | 9.11 |
| R349K | 10.15 |
| Q352E | 32.96 |
| V375D | 5.36 |
| R376T | 2.74 |
| I380M | 2.95 |
| F36Y and N38K | 11.74 |

Four transformants expressing variant LYS20 polypeptides were selected for further analysis. Total protein produced by the strains after a 48 hr growth in poor media was hydrolyzed using a 24 hr treatment at 110° C. with 6 N HCl (Zumwalt, R. W. et al. (1987) *J. Assoc. Off Anal. Chem.* 70:147-51). Samples were analyzed for total amino acid composition and in particular lysine content following derivatization using o-phthalaldehyde, as described. Derivatized lysine was measured as above and the results summarized in Table 3. Lysine increase is reported with reference to the wild-type FG strains. Yeast expressing variant LYS20 polypeptides produced 1.5 to 2.7-fold more protogenic lysine compared to the unmodified FG reference strain.

TABLE 3

Fold increase of proteogenic lysine produced by LYS20 variant yeast

| Mutation | Fold increase |
| --- | --- |
| FG | na |
| FG N38K | 2.10 |
| FG N289D | 1.50 |
| FG R349K | 1.58 |
| FG Q352E | 2.69 |

Example 2: Increased Production of Lysine by Yeast Expressing Variant LYS21 Polypeptides The experiments described in Example 1 were partially repeated with respect to the gene encoding LYS21. Using standard molecular biology techniques, thousands of random mutations in the *S. cerevisiae* gene YDL131w encoding the homocitrate synthase polypeptide LYS21. The resulting library was screened as described, above.

Procedures were based on the nucleic acid sequence of YDL131w (LYS21, chr IV: 227393 . . . 228715), show below as SEQ ID NO: 3:

```
ATGTCTGAAAATAACGAATTCCAGAGTGTCACCGA
ATCGACGACTGCTCCAACCACTAGTAACCCATATG
GCCCAAATCCTGCGGATTATCTATCCAATGTTAAG
AATTTCCAGTTGATTGATTCAACACTAAGAGAGGG
TGAACAATTTGCCAACGCATTCTTCGATACTGAAA
AAAAGATTGAAATTGCTAGAGCCTTGGATGATTTC
GGTGTGGACTACATCGAGTTAACCTCTCCCGTAGC
ATCCGAACAATCAAGAAAGGACTGTGAAGCTATAT
GTAAACTAGGTTTAAAGGCCAAGATCCTTACACAC
ATTCGTTGTCACATGGACGATGCCAGAGTCGCCGT
AGAGACTGGTGTCGACGGTGTCGATGTTGTTATCG
GCACCTCCAAATTTTTAAGACAATATTCCCACGGT
AAGGATATGAACTACATCGCCAAGAGTGCTGTTGA
AGTCATTGAATTTGTCAAATCCAAAGGTATTGAAA
TCAGATTTTCCTCTGAAGATTCCTTCAGAAGTGAT
CTCGTTGATCTTTTGAACATTTATAAAACCGTTGA
CAAGATCGGTGTAAATAGAGTCGGTATTGCCGACA
CAGTTGGATGTGCCAACCCAAGACAAGTATATGAA
CTGATCAGAACTTTGAAGAGTGTTGTCTCATGTGA
CATCGAATGCCATTTCCACAATGATACCGGTTGTG
CCATTGCAAACGCCTACACTGCTTTGGAAGGTGGT
GCCAGATTGATTGACGTCAGTGTACTGGGTATTGG
TGAAAGAAACGGTATCACTCCTCTAGGTGGGCTCA
TGGCAAGAATGATTGTTGCCGCACCAGACTATGTC
AGATCTAAATACAAGCTGCACAAGATCAGAGACAT
CGAAAACCTGGTCGCTGATGCTGTGGAAGTTAACA
TTCCATTCAACAACCCTATCACCGGGTTCTGTGCA
TTCACACATAAAGCAGGTATCCATGCCAAGGCCAT
TTTGGCTAACCCATCTACCTACGAAATCTTGGACC
CTCACGATTTCGGTATGAAGAGGTATATCCACTTC
GCCAACAGACTAACTGGTTGGAATGCAATCAAATC
AAGAGTCGACCAATTGAACTTGAATTTGACGGATG
ATCAAATCAAGGAAGTTACTGCTAAGATTAAGAAG
CTGGGTGATGTCAGACCGCTAAATATTGATGATGT
AGACTCCATTATCAAGGACTTCCATGCAGAATTGA
GCACCCCACTTTTAAAACCAGTAAATAAGGGTACA
GATGACGACAATATCGATATTTCCAATGGGCATGT
TTCTAAAAAGGCAAAGGTCACCAAATAG
```

YDL131w encode the homocitrate synthase polypeptide LYS21 (Genbank Accession No. AY692941) shown below as SEQ ID NO: 1:

```
MSENNEFQSV TESTTAPTTS NPYGPNPADY
LSNVKNFQLI DSTLREGEQF ANAFFDTEKK
IEIARALDDF GVDYIELTSP VASEQSRKDC
EAICKLGLKA KILTHIRCHM DDARVAVETG
VDGVDVVIGT SKFLRQYSHG KDMNYIAKSA
VEVIEFVKSK GIEIRFSSED SFRSDLVDLL
NIYKTVDKIG VNRVGIADAV GCANPRQVYE
LIRTLKSVVS CDIECHFHND TGCAIANAYT
ALEGGARLID VSVLGIGERN GITPLGGLMA
RMIVAAPDYV RSKYKLHKIR DIENLVADAV
EVNIPFNNPI TGFCAFTHKA GIHAKAILAN
PSTYEILDPH DFGMKRYIHF ANRLTGWNAI
KSRVDQLNLN LTDDQIKEVT AKIKKLGDVR
PLNIDDVDSI IKDFHAELST PLLKPVNKGT
DDDNIDISNG HVSKKAKVTK
```

Intracellular free lysine content (mM) was measured as before after 24 hr growth in poor media and analyzed by HPLC. The results are summarized in Table 4. Yeast expressing variants of LYS21 produced 60 to 350-fold more free intracellular lysine compared to the unmodified FG reference strain.

Free intracellular lysine produced by in variant LYS21 transformants Mutation Lysine Fold increase

| Mutation | Lysine | Fold increase |
|---|---|---|
| FG | 0.6 | na |
| N52D | 65.8 | 114 |

-continued

| Mutation | Lysine | Fold increase |
|---|---|---|
| D125N | 202.7 | 353 |
| R289I | 35.1 | 61 |
| N303D | 65.9 | 114 |
| N393D | 99.1 | 172 |

What is claimed is:

1. A non-naturally-occurring variant homocitrate synthase polypeptide having at least 80% amino acid sequence identity to SEQ ID NO: 2 and comprising one or more mutations selected from the group consisting of F36Y, N38K, N289D, R349K, Q352E, V375D, R376T and I380M, with respect to SEQ ID NO: 2, wherein the variant homocitrate synthase polypeptide demonstrates reduced lysine inhibition compared to an otherwise identical homocitrate synthase polypeptide lacking the one or more mutations.

2. Yeast cells producing the variant homocitrate synthase polypeptide of claim 1.

3. The yeast cells of claim 2, wherein the cells are of a *Saccharomyces* spp.

4. The yeast cells of claim 2, wherein the cells further comprise one or more genes of the phosphoketolase pathway.

5. The yeast cells of claim 4, wherein the genes of the phosphoketolase pathway are selected from the group consisting of phosphoketolase, phosphotransacetylase and acetylating acetyl dehydrogenase.

6. The yeast cells of claim 2, wherein the cells further comprise an exogenous gene encoding a carbohydrate processing enzyme.

7. The yeast cells of claim 2, further comprising an alteration in the glycerol pathway and/or the acetyl-CoA pathway.

8. The yeast cells of claim 2, further comprising an alternative pathway for making ethanol.

9. The yeast cells of claim 2, further producing a non-naturally-occurring variant homocitrate synthase polypeptide having at least 80% amino acid sequence identity to SEQ ID NO: 1 and comprising one or more mutations selected from the group consisting of N52D, D125N, R289I, N303D and N393D, with respect to SEQ ID NO: 1, wherein the variant homocitrate synthase polypeptide demonstrates reduced lysine inhibition compared to an otherwise identical homocitrate synthase polypeptide lacking the one or more mutations.

* * * * *

SEQUENCE LISTING

<160> NUMBER OF SEQ ID NOS: 4

<210> SEQ ID NO 1
<211> LENGTH: 440
<212> TYPE: PRT
<213> ORGANISM: Saccharomyces cerevisiae
<220> FEATURE:
<221> NAME/KEY: MISC_FEATURE
<223> OTHER INFORMATION: YDL131w Homocitrate synthase polypeptide LYS21

<400> SEQUENCE: 1

```
Met Ser Glu Asn Asn Glu Phe Gln Ser Val Thr Glu Ser Thr Thr Ala
1               5                   10                  15

Pro Thr Thr Ser Asn Pro Tyr Gly Pro Asn Pro Ala Asp Tyr Leu Ser
                20                  25                  30

Asn Val Lys Asn Phe Gln Leu Ile Asp Ser Thr Leu Arg Glu Gly Glu
            35                  40                  45

Gln Phe Ala Asn Ala Phe Phe Asp Thr Glu Lys Lys Ile Glu Ile Ala
        50                  55                  60

Arg Ala Leu Asp Asp Phe Gly Val Asp Tyr Ile Glu Leu Thr Ser Pro
65                  70                  75                  80

Val Ala Ser Glu Gln Ser Arg Lys Asp Cys Glu Ala Ile Cys Lys Leu
                85                  90                  95

Gly Leu Lys Ala Lys Ile Leu Thr His Ile Arg Cys His Met Asp Asp
            100                 105                 110

Ala Arg Val Ala Val Glu Thr Gly Val Asp Gly Val Asp Val Val Ile
        115                 120                 125

Gly Thr Ser Lys Phe Leu Arg Gln Tyr Ser His Gly Lys Asp Met Asn
    130                 135                 140

Tyr Ile Ala Lys Ser Ala Val Glu Val Ile Glu Phe Val Lys Ser Lys
145                 150                 155                 160

Gly Ile Glu Ile Arg Phe Ser Ser Glu Asp Ser Phe Arg Ser Asp Leu
                165                 170                 175

Val Asp Leu Leu Asn Ile Tyr Lys Thr Val Asp Lys Ile Gly Val Asn
            180                 185                 190

Arg Val Gly Ile Ala Asp Ala Val Gly Cys Ala Asn Pro Arg Gln Val
        195                 200                 205

Tyr Glu Leu Ile Arg Thr Leu Lys Ser Val Val Ser Cys Asp Ile Glu
    210                 215                 220

Cys His Phe His Asn Asp Thr Gly Cys Ala Ile Ala Asn Ala Tyr Thr
225                 230                 235                 240

Ala Leu Glu Gly Gly Ala Arg Leu Ile Asp Val Ser Val Leu Gly Ile
                245                 250                 255

Gly Glu Arg Asn Gly Ile Thr Pro Leu Gly Gly Leu Met Ala Arg Met
            260                 265                 270

Ile Val Ala Ala Pro Asp Tyr Val Arg Ser Lys Tyr Lys Leu His Lys
        275                 280                 285
```

```
Ile Arg Asp Ile Glu Asn Leu Val Ala Asp Ala Val Glu Val Asn Ile
    290                 295                 300

Pro Phe Asn Asn Pro Ile Thr Gly Phe Cys Ala Phe Thr His Lys Ala
305                 310                 315                 320

Gly Ile His Ala Lys Ala Ile Leu Ala Asn Pro Ser Thr Tyr Glu Ile
                325                 330                 335

Leu Asp Pro His Asp Phe Gly Met Lys Arg Tyr Ile His Phe Ala Asn
                340                 345                 350

Arg Leu Thr Gly Trp Asn Ala Ile Lys Ser Arg Val Asp Gln Leu Asn
                355                 360                 365

Leu Asn Leu Thr Asp Asp Gln Ile Lys Glu Val Thr Ala Lys Ile Lys
    370                 375                 380

Lys Leu Gly Asp Val Arg Pro Leu Asn Ile Asp Asp Val Asp Ser Ile
385                 390                 395                 400

Ile Lys Asp Phe His Ala Glu Leu Ser Thr Pro Leu Leu Lys Pro Val
                405                 410                 415

Asn Lys Gly Thr Asp Asp Asn Ile Asp Ile Ser Asn Gly His Val
                420                 425                 430

Ser Lys Lys Ala Lys Val Thr Lys
        435                 440

<210> SEQ ID NO 2
<211> LENGTH: 428
<212> TYPE: PRT
<213> ORGANISM: Saccharomyces cerevisiae
<220> FEATURE:
<221> NAME/KEY: MISC_FEATURE
<223> OTHER INFORMATION: YDL182w Homocitrate synthase polypeptide LYS20

<400> SEQUENCE: 2

Met Thr Ala Ala Lys Pro Asn Pro Tyr Ala Ala Lys Pro Gly Asp Tyr
1               5                   10                  15

Leu Ser Asn Val Asn Asn Phe Gln Leu Ile Asp Ser Thr Leu Arg Glu
            20                  25                  30

Gly Glu Gln Phe Ala Asn Ala Phe Phe Asp Thr Glu Lys Lys Ile Glu
        35                  40                  45

Ile Ala Arg Ala Leu Asp Asp Phe Gly Val Asp Tyr Ile Glu Leu Thr
    50                  55                  60

Ser Pro Val Ala Ser Glu Gln Ser Arg Lys Asp Cys Glu Ala Ile Cys
65                  70                  75                  80

Lys Leu Gly Leu Lys Ala Lys Ile Leu Thr His Ile Arg Cys His Met
                85                  90                  95

Asp Asp Ala Lys Val Ala Val Glu Thr Gly Val Asp Gly Val Asp Val
                100                 105                 110

Val Ile Gly Thr Ser Lys Phe Leu Arg Gln Tyr Ser His Gly Lys Asp
            115                 120                 125

Met Asn Tyr Ile Ala Lys Ser Ala Val Glu Val Ile Glu Phe Val Lys
            130                 135                 140

Ser Lys Gly Ile Glu Ile Arg Phe Ser Ser Glu Asp Ser Phe Arg Ser
145                 150                 155                 160

Asp Leu Val Asp Leu Leu Asn Ile Tyr Lys Thr Val Asp Lys Ile Gly
                165                 170                 175

Val Asn Arg Val Gly Ile Ala Asp Thr Val Gly Cys Ala Asn Pro Arg
            180                 185                 190

Gln Val Tyr Glu Leu Ile Arg Thr Leu Lys Ser Val Val Ser Cys Asp
        195                 200                 205
```

Ile Glu Cys His Phe His Asn Asp Thr Gly Cys Ala Ile Ala Asn Ala
    210                 215                 220

Tyr Thr Ala Leu Glu Gly Gly Ala Arg Leu Ile Asp Val Ser Val Leu
225                 230                 235                 240

Gly Ile Gly Glu Arg Asn Gly Ile Thr Pro Leu Gly Gly Leu Met Ala
            245                 250                 255

Arg Met Ile Val Ala Ala Pro Asp Tyr Val Lys Ser Lys Tyr Lys Leu
                260                 265                 270

His Lys Ile Arg Asp Ile Glu Asn Leu Val Ala Asp Ala Val Glu Val
            275                 280                 285

Asn Ile Pro Phe Asn Asn Pro Ile Thr Gly Phe Cys Ala Phe Thr His
290                 295                 300

Lys Ala Gly Ile His Ala Lys Ala Ile Leu Ala Asn Pro Ser Thr Tyr
305                 310                 315                 320

Glu Ile Leu Asp Pro His Asp Phe Gly Met Lys Arg Tyr Ile His Phe
                325                 330                 335

Ala Asn Arg Leu Thr Gly Trp Asn Ala Ile Lys Ala Arg Val Asp Gln
            340                 345                 350

Leu Asn Leu Asn Leu Thr Asp Asp Gln Ile Lys Glu Val Thr Ala Lys
355                 360                 365

Ile Lys Lys Leu Gly Asp Val Arg Ser Leu Asn Ile Asp Asp Val Asp
370                 375                 380

Ser Ile Ile Lys Asn Phe His Ala Glu Val Ser Thr Pro Gln Val Leu
385                 390                 395                 400

Ser Ala Lys Lys Asn Lys Asn Asp Ser Asp Val Pro Glu Leu Ala
                405                 410                 415

Thr Ile Pro Ala Ala Lys Arg Thr Lys Pro Ser Ala
            420                 425

<210> SEQ ID NO 3
<211> LENGTH: 1323
<212> TYPE: DNA
<213> ORGANISM: Saccharomyces cerevisiae
<220> FEATURE:
<221> NAME/KEY: misc_feature
<223> OTHER INFORMATION: YDL131w LYS21, chr IV: 227393..228715

<400> SEQUENCE: 3

| | |
|---|---|
| atgtctgaaa ataacgaatt ccagagtgtc accgaatcga cgactgctcc aaccactagt | 60 |
| aacccatatg gcccaaatcc tgcggattat ctatccaatg ttaagaattt ccagttgatt | 120 |
| gattcaacac taagagaggg tgaacaattt gccaacgcat tcttcgatac tgaaaaaaag | 180 |
| attgaaattg ctagagcctt ggatgatttc ggtgtggact catcgagtt aacctctccc | 240 |
| gtagcatccg aacaatcaag aaaggactgt gaagctatat gtaaactagg tttaaaggcc | 300 |
| aagatcctta cacacattcg ttgtcacatg gacgatgcca gagtcgccgt agagactggt | 360 |
| gtcgacggtg tcgatgttgt tatcggcacc tccaaatttt taagacaata ttcccacggt | 420 |
| aaggatatga actacatcgc caagagtgct gttgaagtca ttgaatttgt caaatccaaa | 480 |
| ggtattgaaa tcagattttc ctctgaagat tccttcagaa gtgatctcgt tgatcttttg | 540 |
| aacatttata aaccgttga caagatcggt gtaaatagag tcggtattgc cgacacagtt | 600 |
| ggatgtgcca acccaagaca agtatatgaa ctgatcagaa cttttgaaga gtgttgtctca | 660 |
| tgtgacatcg aatgccattt ccacaatgat accggttgtg ccattgcaaa cgcctacact | 720 |
| gctttggaag gtggtgccag attgattgac gtcagtgtac tgggtattgg tgaaagaaac | 780 |

```
ggtatcactc ctctaggtgg gctcatggca agaatgattg ttgccgcacc agactatgtc    840
agatctaaat acaagctgca caagatcaga gacatcgaaa acctggtcgc tgatgctgtg    900
gaagttaaca ttccattcaa caaccctatc accgggttct gtgcattcac acataaagca    960
ggtatccatg ccaaggccat tttggctaac ccatctacct acgaaatctt ggaccctcac   1020
gatttcggta tgaagaggta tatccacttc gccaacagac taactggttg aatgcaatc    1080 aaatcaagag tcgaccaatt gaacttgaat ttgacggatg atcaaatcaa ggaagttact   1140
gctaagatta agaagctggg tgatgtcaga ccgctaaata ttgatgatgt agactccatt   1200
atcaaggact ccatgcagaa attgagcacc ccacttttaa aaccagtaaa taagggtaca   1260 gatgacgcaca atatcgatat ttccaatggg catgtttcta aaaaggcaaa ggtcaccaaa   1320
tag                                                                 1323

<210> SEQ ID NO 4
<211> LENGTH: 1287
<212> TYPE: DNA
<213> ORGANISM: Saccharomyces cerevisiae
<220> FEATURE:
<221> NAME/KEY: misc_feature
<223> OTHER INFORMATION: YDL182w LYS20, chr IV: 133437..134723

<400> SEQUENCE: 4
atgactgctg ctaaaccaaa tccatatgct gccaaaccgg cgactatct ttctaatgta     60 aataatttcc agttaatcga ttcgacgctg agagaaggtg aacaatttgc caacgcattc    120
ttcgatactg aaaaaaagat cgaaattgct agagccttgg acgatttcgg tgtggactac    180
atcgagttaa cctcaccagt agcatctgaa caatcaagaa aggactgtga agctatatgt    240
aaactaggtt taaaggccaa gatccttaca cacattcgtt gtcatatgga tgacgccaaa    300
gtcgccgtag agactggtgt cgacggtgtc gatgtcgtta tcggcacctc caaattttta    360
agacaatatt cccacggtaa ggatatgaac tacatcgcca agagtgctgt tgaagtcatt    420
gaatttgtca aatccaaagg tattgaaatc agatttcct ctgaagattc cttcagaagt    480
gatctcgttg atcttttgaa catttataaa accgttgaca agatcggtgt aaatagagtc    540
ggtattgccg acacagttgg atgtgccaac ccaagacaag tatatgaact gatcagaact    600
ttgaagagtg ttgtttcatg tgacatcgaa tgccatttcc acaacgatac tggttgtgcc    660
atcgcaaacg cctacactgc tttggaaggt ggtgccagat tgattgacgt cagtgtactg    720
ggtattggtg aaagaaacgg tatcactcct ctaggtgggc tcatggcaag aatgattgtt    780
gccgcaccag actatgtcaa gtccaaatac aagttgcaca agatcagaga cattgaaaac    840
ctggtcgctg atgctgtgga agttaacatt ccattcaaca accctatcac cgggttctgt    900
gcattcacac ataaagcagg tatccatgcc aaggccattt tggctaaccc atctacctac    960
gaaatcttgg accctcacga tttcggtatg aagaggtata tccacttcgc caacagacta   1020
actggctgga acgccatcaa agccagagtc gaccagttga acttgaattt gacagatgac   1080
caaatcaagg aagttactgc taagattaag aagctgggtg atgtcagatc gctgaatatc   1140
gatgatgttg actctatcat caagaacttc cacgcagagg tcagcactcc tcaagtacta   1200
tctgcaaaaa agaacaagaa gaatgacagc gatgtaccgg aactggccac catccccgcc   1260
gccaagcgga ctaagccatc cgcctaa                                       1287
```